United States Patent
Ruebenacker et al.

(10) Patent No.: US 11,850,579 B2
(45) Date of Patent: Dec. 26, 2023

(54) CATALYSTS FOR POLYESTEROL SYNTHESIS

(71) Applicant: BASF SE, Ludwigshafen am Rhein (DE)

(72) Inventors: Martin Ruebenacker, Ludwigshafen (DE); Sirus Zarbakhsh, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 1026 days.

(21) Appl. No.: 16/620,936

(22) PCT Filed: Jul. 3, 2018

(86) PCT No.: PCT/EP2018/067870
§ 371 (c)(1),
(2) Date: Dec. 10, 2019

(87) PCT Pub. No.: WO2019/007921
PCT Pub. Date: Jan. 10, 2019

(65) Prior Publication Data
US 2020/0197917 A1    Jun. 25, 2020

(30) Foreign Application Priority Data
Jul. 5, 2017 (EP) .................................... 17179787

(51) Int. Cl.
| | | |
|---|---|---|
| *C08G 18/63* | (2006.01) |
| *C08G 18/42* | (2006.01) |
| *B01J 31/02* | (2006.01) |
| *C07C 67/08* | (2006.01) |
| *C08G 63/68* | (2006.01) |
| *C08G 63/688* | (2006.01) |
| *C08G 63/16* | (2006.01) |

(52) U.S. Cl.
CPC ............. *B01J 31/022* (2013.01); *C07C 67/08* (2013.01); *C08G 18/42* (2013.01); *C08G 63/16* (2013.01); *C08G 63/68* (2013.01); *C08G 63/688* (2013.01); *C08G 63/6886* (2013.01)

(58) Field of Classification Search
CPC .... C08G 63/16; C08G 63/68; C08G 63/6886; C08G 63/688; C08G 63/826; C08G 63/82
See application file for complete search history.

(56) References Cited

U.S. PATENT DOCUMENTS

| | | | |
|---|---|---|---|
| 2,698,340 A | 12/1954 | Mertzweiller | |
| 3,459,787 A * | 8/1969 | Weesner | C08L 27/06 525/437 |
| 3,513,133 A * | 5/1970 | Weesner | C08G 63/6884 525/437 |
| 3,644,291 A | 2/1972 | Price et al. | |
| 3,664,291 A | 5/1972 | Fritz | |
| 4,996,178 A | 2/1991 | Ogata | |
| 2016/0200856 A1 * | 7/2016 | Jimenez | C08G 18/4294 521/131 |

FOREIGN PATENT DOCUMENTS

| | | | | |
|---|---|---|---|---|
| FR | 1.359.112 | | 4/1964 | |
| JP | 2009091410 A | * | 4/2009 | ........... C08G 63/688 |

OTHER PUBLICATIONS

JP-2009091410-A_04-2009_Dobashi et al._English Translation.*
Extended European Search Report dated Nov. 21, 2017 in European Patent Application No. 17179787.1, 3 pages.
Ionescu, M., "Chapter 8.1—Polyester Polyols for Elastic Polyurethanes", Chemistry and Technology of Polyosis for Polyurethanes. Rapra Technology Limited. 2005, pp. 263-270.
International Search Report dated Jul. 31, 2018 in PCT/EP2018/067870 filed on Jul. 3, 2018.
U.S. Appl. No. 16/618,654, filed Dec. 2, 2019, Ruebenacker, M., et al.

* cited by examiner

*Primary Examiner* — Michael L Leonard
(74) *Attorney, Agent, or Firm* — Grüneberg and Myers PLLC

(57) ABSTRACT

This invention relates to catalysts for polyesterol synthesis and the use of a di-thio compound as catalyst for the production of polyester-polyols.

10 Claims, 1 Drawing Sheet

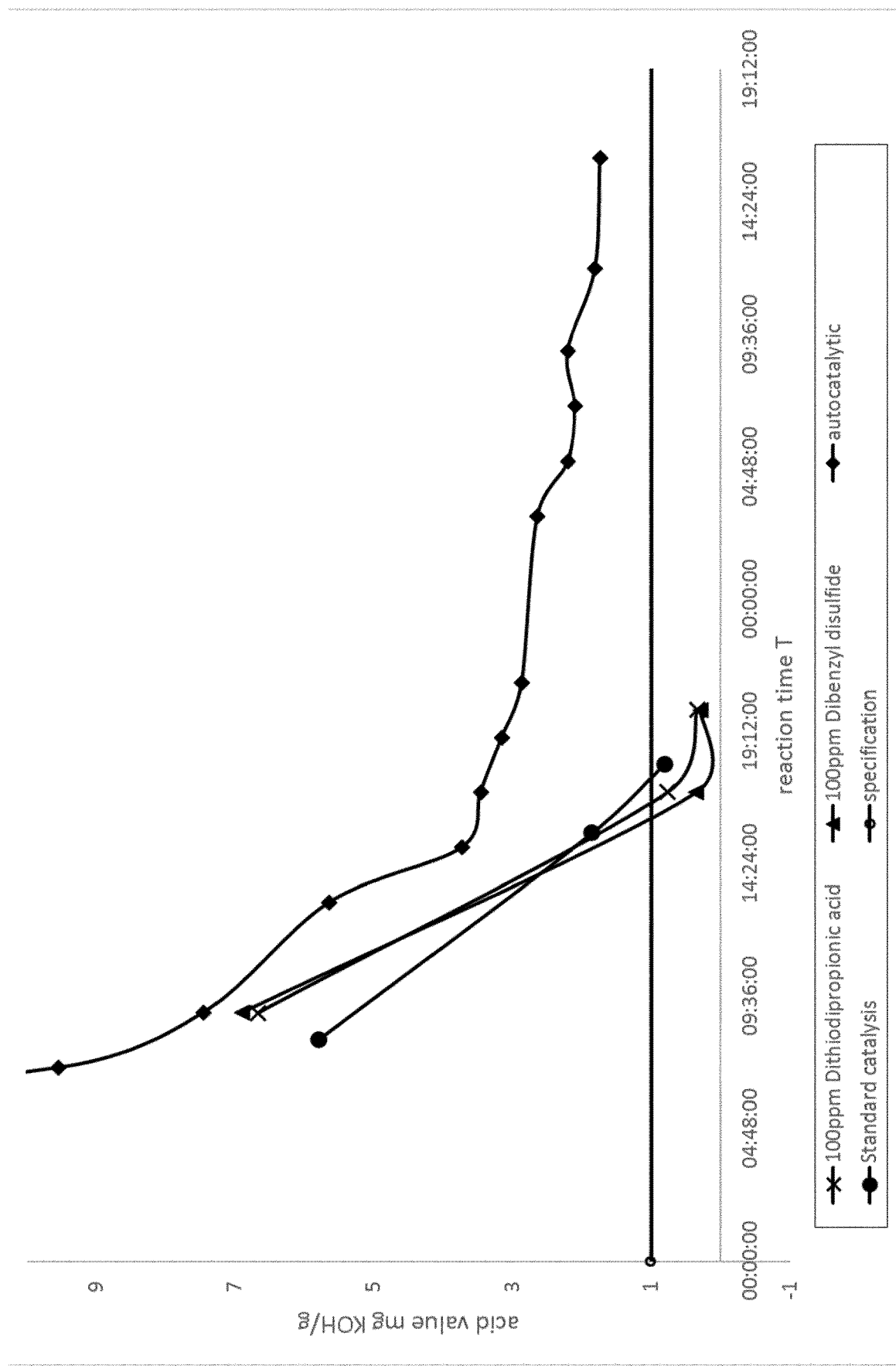

CATALYSTS FOR POLYESTEROL SYNTHESIS

This invention relates to catalysts for polyesterol synthesis and the use of a di-thio compound as catalyst for the production of polyester-polyols.

In principal, catalysts for the production of esters are widely known in the art. For example, FR 1359112 describes the use of tin catalysts for the production of di-esters based on tin-catalyts, wherein for example di-thioproprinic acid is used as educt for esterification of small compounds.

In the present invention, the term "catalyst" refers to a compound that increases the reaction rate of a chemical reaction. Differing from the usual definition of the term "catalyst", the inventive compound may (at least in part) be consumed by (chemical) incorporation into the product. Thus, the polyesterol product may contain traces of the catalyst compound.

Polyesterols (also called "polyester polyols" or short "PESOLs") are a well-known class of compounds which can, for example, be used in the synthesis of polyurethanes (PU).

Polyesterols are obtained by the polycondensation reactions between dicarboxylic acids (or derivatives such as esters or anhydrides) and diols (or polyols), or by the ring opening polymerization of cyclic esters (e. g. lactones, cyclic carbonates); this is, for example, described in M. Ionescu, "Chemistry and technology of polyols for polyurethanes", Rapra Technology Ltd., 2005, chapter 8.1.

Polyesterols are generally produced using metal complexes as catalyst. The most common catalysts are based on titanium or tin (for example tetrabutyltitanate or stannous octoate). TTB and SDO show a high reactivity and enable short cycle times; these catalysts are usually not separated from the product.

However, for many applications of polyesterols, for example food- or medical-related applications, it is a big disadvantage if the product contains traces of metal from the catalyst. If the metal catalysts remain in the polyol they are still catalytically active and influence the reactivity in the polyurethane reaction in a negative way (they actually increase the reactivity which is not desired). The metal catalyst does at the same time induce the back reaction of the polyol to the diacid and the diol and therefore reduce the hydrolysis resistance of the polyesterol.

Also from the point of view of ecology and sustainability it is highly desirable to refrain from using metal-containing catalysts. Unfortunately, though, metal free catalyst systems with sufficiently high reactivity for the production of polyesterols are not known in the art.

U.S. Pat. No. 2,698,340 discloses the use of sulfur-containing catalysts, preferably lauryl mercaptan, n-heptyl mercaptan or iso-octyl mercaptan, in a process for the preparation of esters, which may be used as plasticizers for various resins. However, high quantities of the catalytically active compound are required. Furthermore, thiols are known to have a bad smell which is not acceptable for most applications.

t has also been described to use p-toluene sulfonic acid as catalyst for the manufacture of PESOLs, but also in this case, very high amounts of the acid compound are required, making this procedure uneconomical and unecological. There was therefore a need in the art for compounds which can be used efficiently as catalyst in the production of polyesterols and do not contain metals.

Other catalytic systems have the disadvantage that they are based on e.g. halogenated organic compounds, which use should be avoided in view of environmentally friendly production. For example, U.S. Pat. No. 4,996,178 describes a catalyst system based on a phosphorous compound, an acid receptor and at least one halogenated compound.

It has now surprisingly been found that specific di-thio structures, like 3,3'-dithiopropionic acid or dibenzyldisulfide, are highly active catalysts for the synthesis of polyesterols.

Furthermore, when using the inventive catalytic structures, the resulting products do not show an increased reactivity for example in TPU formation.

Besides, due to the metal-free structure of the inventive catalyst compounds, the products are free from traces of metal, and have almost no smell.

Thus, an object of the present invention is the use of a compound containing structural element —$CH_2$—S—S—$CH_2$— as catalyst for the production of polyesterols.

Further objects of the present invention are also a process for the production of a polyesterol by reaction of at least one di-carboxylic acid with at least one diol or polyol, wherein at least one compound containing structural element —$CH_2$—S—S—$CH_2$— is used as a catalyst, and the use of a polyesterol, obtainable from the inventive process, for the production of polyurethanes.

In an embodiment of the invention, the compound containing structural element —$CH_2$—S—S—$CH_2$— is a compound of formula I $$R1\text{-}CH_2\text{—S—S—}CH_2\text{-}R2 \qquad (I),$$

wherein R1 is selected from the group consisting of Ar1 and —$(CH_2)_x$—COOH, wherein x is selected from 0, 1, 2, or 3, and wherein R2 is selected from the group consisting of Ar2 and —$(CH_2)_y$—COOH, wherein y is selected from 0, 1, 2, or 3.

Ar1 and Ar2 independently from each other stand for substituted or un-substituted phenyl, preferably unsubstituted phenyl, wherein, if substituted, the substituent is one or more $C_1$-$C_4$ alkyl.

The term $C_1$-$C_4$ alkly includes methyl, ethyl, propyl, 1-methylethyl, butyl, 1-methylpropyl, 2-methylpropyl, 1,1-dimethylethyl, In one preferred embodiment of the present invention, in formula I
R1 is —$(CH_2)_x$—COOH,
x is 0, 1, 2 or 3;
R2 is —$(CH_2)_y$—COOH and y is 0, 1, 2, or 3 (hereinafter referred to as formula Ia).

In an equally preferred embodiment of the present invention, in formula I
R1 and R2 both are phenyl substituted by one to three $C_1$-$C_4$ radicals or un-substituted phenyl ((hereinafter referred to as formula Ib).

In a more preferred embodiment of the present invention, in formula I
R1 is —$(CH_2)_x$—COOH,
x is 0, 1, 2 or 3;
R2 is —$(CH_2)_y$—COOH,
y is 0, 1, 2, or 3, wherein x and y have the same value (e.g. x=1 means y=1) (hereinafter referred to as formula Ic).

In an equally preferred embodiment of the present invention, in formula I R1 and R2 both are unsubstituted phenyl (hereinafter referred to as formula Id).

In a preferred embodiment of formula Ia, x and y are, independently from each other, 1 or 2, preferably 1.

In a preferred embodiment formula Ic, x and y are equally 1 or 2, preferably 1.

Thus, in a particular preferred embodiment of this invention, the compound of formula I is 3,3'-dithiopropionic acid.

In another preferred embodiment of this invention (formula Id), the compound of formula I is dibenzyldisulfide.

A further embodiment of the present invention is also a process for the production of a polyesterol, wherein at least one compound of structural formula I

$$R1\text{-}CH_2\text{---}S\text{---}S\text{---}CH_2\text{-}R2 \qquad (I)$$

is used as catalyst, wherein R1 is selected from the group consisting of Ar1 and —$(CH_2)_x$—COOH, wherein x is selected from 0, 1, 2, or 3, and wherein R2 is selected from the group consisting of Ar2 and —$(CH_2)_y$—COOH, wherein y is selected from 0, 1, 2, or 3 and Ar1 and Ar 2 are as defined above.

In a preferred embodiment of the process for the production of a polyesterol a compound of formula Ia or Ib is used, more preferably a compound of formula Ic or formula Id, most preferably ibenzyldisulfide or 3,3'-dithiopropionic acid.

In the inventive process the amount of compound I in the reaction is between 1 ppm and $10^4$ ppm (1% by weight).

Preferably, in the inventive process, 1 to 1000 ppm, more preferably 10 to 500 ppm, most preferably 50 to 200 ppm, wherein the range of 70 to 130 ppm of the compound I is utmost preferred.

In an embodiment of the inventive process, the di-carboxylic acid is selected from the group consisting of malonic acid, succinic acid, glutaric acid, adipic acid and pimelic acid, preferably from the group consisting of succinic acid, glutaric acid and adipic acid, more preferably adipic acid.

In an embodiment of the inventive process, the diol is selected from the group consisting of monoethylene glycol, diethylene glycol, propane diol, 1,4-butane diol, trimethylol propane (TMP), preferably monethylene glycol and/or 1,4-butane diol.

Usually the reaction is performed at a temperature between 80° and 300° C., preferably 100° C. and 280° C.

Further embodiments of the present invention are evident from this specification and the independent and dependent claims.

EXAMPLES

Determination of Viscosity

The viscosity of the polyols was determined at 25° C. according to DIN EN ISO 3219 (1994) with a rotational viscosimeter Rheotec RC 20, using spindle CC 25 DIN (diameter of spindle: 12.5 mm; interior diameter of measuring cylinder: 13.56 mm) at a shear rate of 50 l/s.

Determination of Hydroxyl Number

The hydroxyl number were determined according to the phthalic anhydride method DIN 53240 (1971-12) and are given in mg KOH/g.

Determination of the Acid Number

The acid number was determined according to DIN EN 1241 (1998-05) and is given in mg KOH/g.

Synthesis of the Polyols

The following catalysts were used:
Titanium(IV) butoxide CAS: 5593-70-4 (TTB)
Tin(II) 2-ethylhexanoate CAS: 301-10-0 (SDO)

Example 1 (Comparison, Standard Catalysis)

A 4 l flask equipped with thermometer, nitrogen inlet, heating mantle, distillation column and stirrer was charged with 1887.6 g of 1,6-hexanoic diacid (adipic acid), 452.8 g of monoethylene glycol, 657.4 g of 1,4-butane diol and 25 mg of titanium(IV)butoxide and heated to 120° C. The reaction mixture was further heated to 240° C. and the condensation water was continuously distilled off until an acid number of 1 mg KOH/g was reached. A polyester polyol with a hydroxyl number of 53.26 mg KOH/g, an acid number of 0.708 mg KOH/g and a viscosity of 738 mPas at 75° C. was obtained.

Example 2 (Dithio Propionic Acid)

A 4 l flask equipped with thermometer, nitrogen inlet, heating mantle, distillation column and stirrer was charged with 1887.7 g of 1,6-hexanoic diacid (adipic acid), 452.8 g of monoethylene glycol, 657.4 g of 1,4-butane diol and 250 mg of 3,3-dithio propionic acid and heated to 120° C. The reaction mixture was further heated to 240° C. and the condensation water was continuously distilled off until an acid number of 1 mg KOH/g was reached. A polyester polyol with a hydroxyl number of 55.66 mg KOH/g, an acid number of 0.292 mg KOH/g and a viscosity of 974.3 mPas at 75° C. was obtained.

Example 3 (Dibenzyldidisulfide)

A 4 l flask equipped with thermometer, nitrogen inlet, heating mantle, distillation column and stirrer was charged with 1887.7 g of 1,6-hexanoic diacid (adipic acid), 452.8 g of monoethylene glycol, 657.4 g of 1,4-butane diol and 250 mg of dibenzyldisulfide and heated to 120° C. The reaction mixture was further heated to 240° C. and the condensation water was continuously distilled off until an acid number of 1 mg KOH/g was reached. A polyester polyol with a hydroxyl number of 56.38 mg KOH/g, an acid number of 0.339 mg KOH/g and a viscosity of 849.2 mPas at 75° C. was obtained.

Example 4 (Autocatalytic)

A 4 l flask equipped with thermometer, nitrogen inlet, heating mantle, distillation column and stirrer was charged with 1887.7 g of 1,6-hexanoic diacid (adipic acid), 452.8 g of monoethylene glycol, 657.4 g of 1,4-butane diol and 250 mg of dibenzyldisulfide and heated to 120° C. The reaction mixture was further heated to 240° C. and the condensation water was continuously distilled off until an acid number of 2 mg KOH/g was reached. A polyester polyol with a hydroxyl number of 52 mg KOH/g and an acid number of 1.73 mg KOH/g and a viscosity of 889.4 mPas at 75° C. was obtained.

The examples show that the inventive compounds may be used as catalysts in the manufacture of polyesterols.

FIG. 1 shows reaction kinetic data of polyesterol synthesis experiments with different catalysts. It can be seen that the use of the inventive, sulfur-containing compounds results in faster reactions, thus the inventive sulfur-containing compounds have a catalytic activity in the manufacture of polyesterols.

The invention claimed is:

1. A process of producing a polyesterol, the process comprising:
catalyzing a reaction with a compound of formula I

$$R1\text{-}CH_2\text{---}S\text{---}S\text{---}CH_2\text{-}R2 \qquad (I),$$

wherein R1 is selected from the group consisting of Ar1 and —$(CH_2)_x$—COOH,
wherein x is 0, 1, 2 or 3; and R2 is selected from the group consisting
of Ar2 and —(CH$_2$)$_y$—COOH, wherein y is 0, 1, 2 or 3,
wherein Ar1 and Ar2 are substituted or unsubstituted phenyl;
wherein said reaction is a reaction of at least one di-carboxylic acid with at least one diol or polyol; and
wherein an amount of the compound of formula I in a reaction mixture is between 1 to $10^4$ ppm.

2. The process of claim 1, wherein R1 is —(CH2)x-COOH, wherein x is 0, 1, 2 or 3; and R2 is —(CH2)y-COOH, wherein y is 0, 1, 2 or 3.

3. The process of claim 1, wherein R1 is Ar1 and R2 is Ar2.

4. The process of claim 1, wherein x and y are 1.

5. The process of claim 1, wherein R1 and R2 are unsubstituted phenyl.

6. The process of claim 1, wherein an amount of the compound of formula I in a reaction mixture is between 1 to $10^3$ ppm.

7. The process of claim 1, wherein the at least one di-carboxylic acid is selected from the group consisting of malonic acid, succinic acid, glutaric acid, adipic acid and pimelic acid.

8. The process of claim 1, wherein the at least one diol is selected from the group consisting of monoethylene glycol, diethylene glycol, propane diol, 1,4-butane diol, and trimethylol propane (TMP).

9. The process of claim 1, wherein the reaction is performed at a temperature between 80° and 300° C.

10. A process of producing a polyurethane, the process comprising reacting a polyesterol obtainable from the process of claim 1.

* * * * *